United States Patent [19]
Bonaldo

[11] Patent Number: 5,947,954
[45] Date of Patent: Sep. 7, 1999

[54] NEEDLE-LESS LUER ACTUATED MEDICAL CONNECTOR

[75] Inventor: Jean M. Bonaldo, Upland, Calif.

[73] Assignee: Creative Plastic Technology, LLC, Upland, Calif.

[21] Appl. No.: 08/974,332

[22] Filed: Nov. 19, 1997

[51] Int. Cl.[6] .............................. A61M 25/00; A61M 5/00
[52] U.S. Cl. ........................... 604/533; 604/248; 604/905
[58] Field of Search ..................................... 604/246, 248, 604/533, 537, 905; 251/149.1

[56] References Cited

U.S. PATENT DOCUMENTS

| | | | |
|---|---|---|---|
| 3,626,980 | 12/1971 | Svensson | 137/614.2 |
| 3,794,042 | 2/1974 | De Klotz et al. | 128/349 R |
| 5,045,068 | 9/1991 | Kawai et al. | 604/246 |
| 5,836,924 | 11/1998 | Kelliher et al. | 604/248 |

*Primary Examiner*—Wynn Wood Coggins
*Assistant Examiner*—Michael J. Hayes
*Attorney, Agent, or Firm*—W. Norman Roth

[57] ABSTRACT

A needle-less three part medical fluid flowline connector comprised of a relatively rotatable male Luer housing and a female Luer valve actuator includes a compressed elastomeric valve element having a fluid passageway therein which extends from an axially aligned end on one side of the valve element to an off-center positioned end on the other side of the valve element and avoids the use of a cannula and septum which is pierced during valve opening. Rotation of the compressible valve element with respect to the housing in which it is seated is prevented by interengaged fingers and grooves on the housing and valve element. Withdrawal of the valve actuator from the housing is prevented by a abutting radially extending surfaces and an annular bulge and groove on the actuator and housing respectively. An interengageable longitudinally extending finger and diametrically spaced grooves on the actuator and housing enable the user to readily position the valve in an open or closed position.

18 Claims, 5 Drawing Sheets

NEEDLE-LESS LUER ACTUATED MEDICAL CONNECTOR

CROSS-REFERENCE TO RELATED APPLICATIONS, IF ANY

None.

BACKGROUND OF THE INVENTION AND PRIOR ART

The present invention relates to medical connectors for blood transfer, intravenous fluid supply, medication dosage and the like.

My prior U.S. Pat. Nos. 5,273,533 issued Dec. 28, 1993 and 5,306,243 issued Apr. 26, 1994 disclose a medical connector valve which employs an elastomeric valve element in the form of an elastomeric septum or fluid barrier disposed in a two part plastic housing. The septum is pierced by an upstream pointed cannula to make the fluid connection. Disconnection of the flow line allows the elastomer to re-seal the connector. Valve opening and closing is regulated by rotating a fluid line connection with respect to a housing in which the cannula and septum are mounted. Such connectors are relatively expensive due to the presence of a cannula and the mounting thereof and are increasingly more likely to leak or become contaminated with particulate material of the septum due to repeated use.

Medical connectors frequently must be repeatedly opened and closed during patient care. In hospital environments such as intensive care units medical connectors may be actuated or cycled many times and must remain leak free so as to safely avoid introduction of contaminants such as cotton fibers from swabs used to clean the connectors and inadvertent introduction of air bubbles which cause embolisms and patient death.

Medical connectors which use resilient flow barriers which are repeatedly pierced during use of the connector become more subject to fluid leakage with increased actuation cycles, particularly if connected in an infusion pump line which may subject the connector to pressures as high as 27 psi.

OBJECTS OF THE INVENTION

It is the primary objective of the invention to provide a medical connector which remains leak and particle free despite repetitive use.

It is a further objective of the invention to provide a reliable and simple medical connector which does not employ a resilient barrier which is repeatedly pierced by a cannula.

It is a further object of the invention to provide a reliable medical connector comprised of as few as three parts, each of which are easily formed in mass production.

SUMMARY OF THE INVENTION

The present invention accordingly provides a needle-less Luer activated medical connector having a longitudinal axis, said connector comprising:

A) a valve housing having a fluid flow passage therein aligned with said longitudinal axis, a valve seat therein, an open end for receiving a compressible valve element and a connection end for connecting said connector to a fluid flow line aligned with said longitudinal axis;

B) a valve actuator having a fluid flow passage therein aligned with said longitudinal axis of said connector, a valve compressing end wall received in said open end of said housing, and a fluid flow passage extending through said end wall, said valve actuator being mounted in said open end of said housing for rotation about said longitudinal axis with respect to said housing;

C) a resilient valve element compressed between said valve seat and said valve compressing end of said actuator, said valve element having a fluid passageway therethrough extending from an axially aligned opening on a first side of said valve element to an off-center positioned opening on an opposite side of said valve element; said off-center positioned opening of said fluid passageway in said valve element being aligned with one of (1) an off-center positioned end of said flow passageway in said valve actuator or (2) an off-center positioned end of said flow passageway in said housing when said actuator is rotated relative to said housing to open said valve and said off-center positioned end of said valve passageway being circumfrentially displaced from (1) said off-center positioned end of said flow passageway in said valve actuator or (2) said off-center positioned end of said flow passageway in said housing when said actuator is rotated relative to said housing to close the valve;

D) means connecting said valve element to said housing to prevent relative rotation between said valve element and said housing;

E) positioning means on said actuator and said housing to hold said actuator in either a valve open position or in a valve closed position relative to said housing; and F) restraining means on said housing and on said actuator for restraining relative axial movement therebetween while permitting relative rotation therebetween.

BRIEF DESCRIPTION OF THE DRAWINGS

In the accompanying drawings:

FIG. 5 is a perspective view of the valve element;

DESCRIPTION OF THE PREFERRED EMBODIMENT

Figure 1:
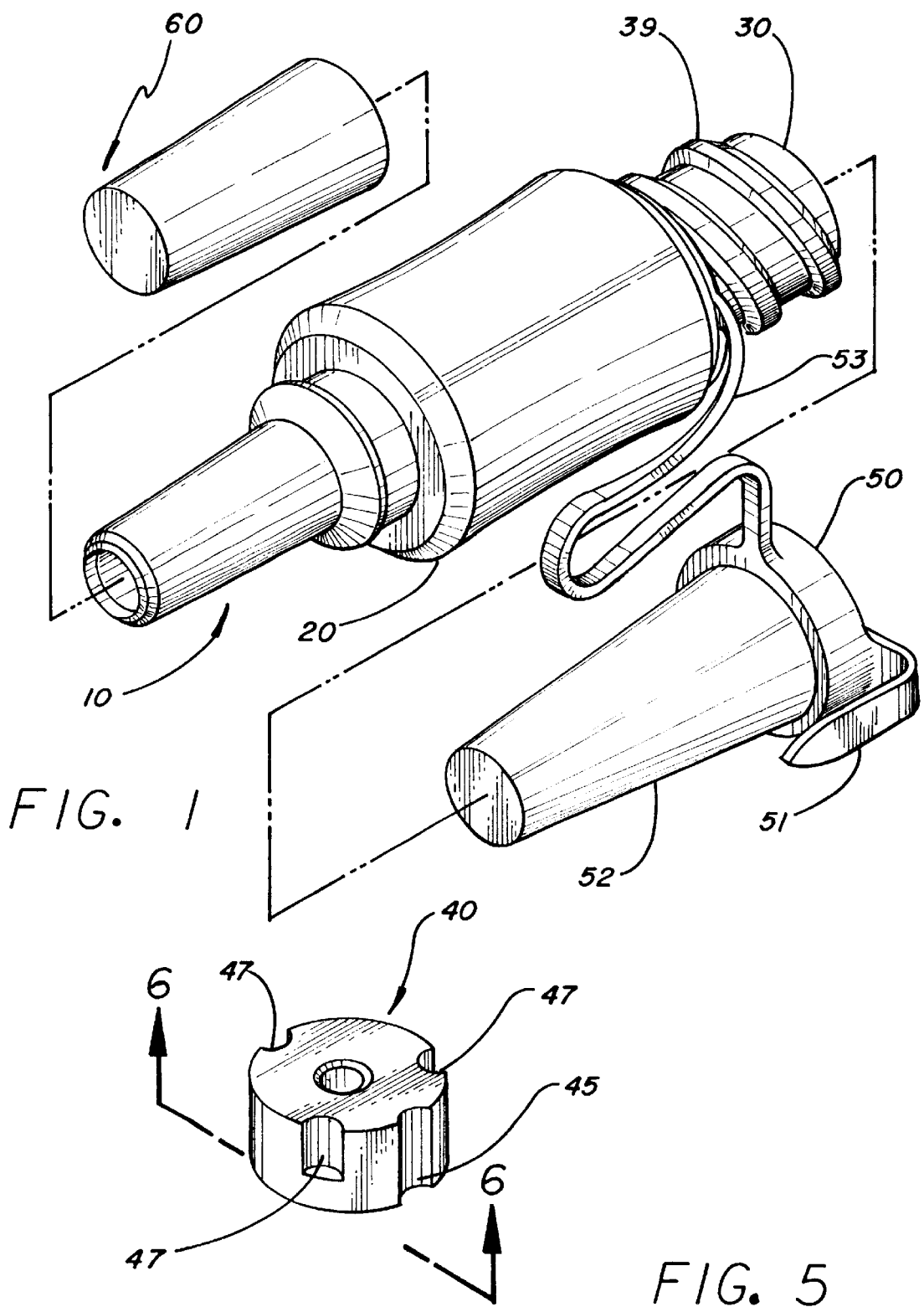
FIG. 1 comprises a perspective view of a medical connector according to the present invention including a contamination cap for a male Luer part and a contamination plug/swab for a female Luer part of the connector.

The medical connector 10 of the present invention is essentially a three part connector comprising a valve housing 20 having a male Luer configured end 26 and a female Luer configured valve actuator 30 with a resilient valve element 40 which is compressed between a planar valve seat 22 in the housing 20 and a planar end wall 32 of the valve actuator 30.

The male Luer housing 20 and female Luer valve actuator 30 are aligned on a common longitudinal axis and are rotatable with respect to each other about the longitudinal axis. A concave gripping surface 21 on the housing 20 facilitates fingertip operation of the connector.

The valve housing 20 has a fluid flow passage 24 therein which extends longitudinally from the male Luer fluid line connection end 26 to the valve seat 22. Similarly, the valve actuator 30 has an axially extending female Luer fluid flow passage 34 therein which, in the embodiment shown, terminates in an off-center positioned flow passage 36 in the end wall 32 of the valve actuator which compressively engages the valve element 40. The actuator 30 is molded to have a smooth curved flow transition from axially extending flow passage 34 to off-center passage 36.

The valve element 40 has a fluid flow passageway 44 extending therethrough from an axially aligned opening in fluid communication with passage 24 to an off-center positioned end 48 which can be placed into or out of flow communication with off-center actuator passage 36. Valve element 40 is made of a firm but compressible elastomer which is compressed between the valve seat 22 in the housing and the end wall 32 of the actuator during assembly of the valve. Axial compression of the elastomeric valve element 40 causes radial expansion of the valve element 40 into fluid tight engagement with the surrounding interior cylindrical wall of the housing 20 to provide a tight seal of the valve in open, closed and intermediate positions.

Restraining means on an interior cylindrical wall 28 proximate the open end of the housing 20 and on an exterior cylindrical wall 38 of the valve actuator in the form of an annular bulge 39 on the actuator and mating receiving groove 29 on the housing are dimensioned such that the valve element 40 is compressed to the appropriate extent as the bulge 39 seats itself in the groove 29 during valve assembly. Axial movement of the valve actuator 30 with respect to the housing 20 is thus prevented during operation of the valve. Preferably, abutting radially extending surfaces on the bulge 39 and groove 29 are provided at the location shown to prevent inadvertent withdrawal of the actuator 30 from the housing 20 after the valve has been assembled. Relative rotation between the housing and actuator is, however, permitted. Preferably, a rigid sleeve 46 is provided in the flow passage 44 in the resilient valve element 40 to minimize radial collapse thereof during axial compression of the valve element as the parts of the medical connector are assembled. Sleeve 46, if provided, also prevents all contact of the elastomeric valve element with fluid flow through the connector thus avoiding any possibility of contamination of the fluid by the elastomer or coagulation of blood or other fluid proximate the elastomer.

Figure 2:
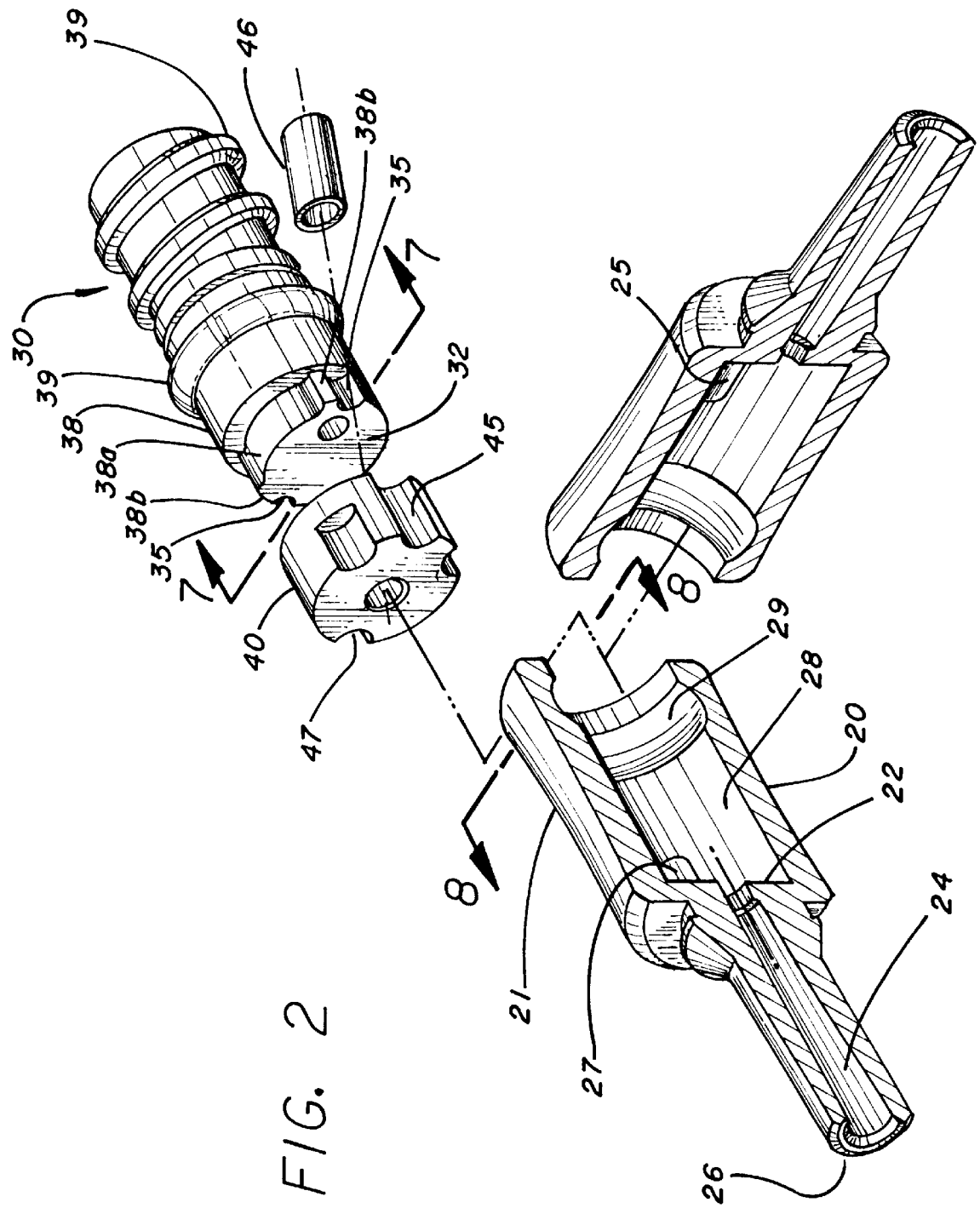
FIG. 2 comprises an exploded perspective view of the medical connector of FIG. 1.
Figure 7:
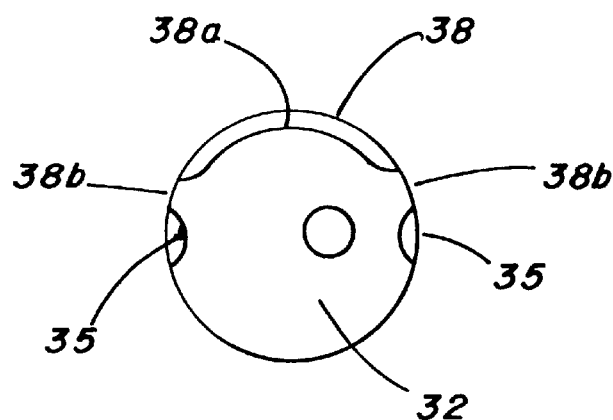
FIG. 7 is an end elevation of a valve contacting end of a valve actuator.
Figure 8:
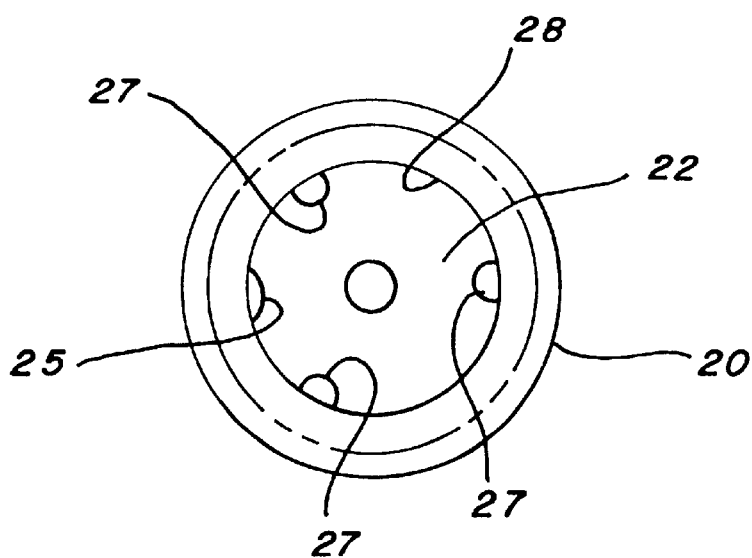
FIG. 8 is a right end elevation of a valve housing.

Valve open and valve closed positioning means in the form of a molded long finger 25 on the housing 20 which is received in one or the other of diametrically opposed finger positioning grooves 35 molded in the actuator 30 hold the actuator relative to the housing in either a valve open position or in a valve closed position. The inherent resiliency of the plastic materials of which the housing 20 and valve actuator 30 are made permit the long finger 25 to snap into one or the other of the grooves 35 when the valve is either in the open or closed position while permitting relatively easy manual rotation of the valve actuator 30 relative to the housing 20. The valve element 40 also has a single longitudinally extending groove 45 which receives the long positioning finger 25 on the housing. As seen in FIGS. 2 and 7, the exterior cylindrical surface 38 on the actuator 30 extends in excess of 180° proximate the grooves 35 to an annular reduced radius recess 38a of approximately the same depth as grooves 35 to permit the long finger 25 to be received in the annular gap between reduced radius recess 38a and interior housing wall 28 as the actuator 30 is rotated clockwise relative to the housing (as viewed from the actuator end) to open the fluid connection. Radially extending protuberances 38b between the grooves 35 and the recess 38a engage the finger 25 but permit movement of the finger 25 over the protuberances 38b as the connector parts are relatively rotated to open or close the valve so as to provide the user with a "feel" to determine if the valve is in its open or closed position. The full radius portion of surface 38 which extends in excess of 180° prevents further clockwise rotation of the actuator 30 relative to the housing by interference with long finger 25 and requires counterclockwise movement of the actuator relative to the housing to close the fluid connection.

Relative rotation between the valve element 40 and the housing 20 is prevented at all times by mating short fingers 27 molded on the housing which are receivable in short longitudinally extending grooves 47 molded in the valve element. Although three short fingers 27 and grooves 47 are provided to prevent relative rotation between the valve element and the housing 20, as will be apparent, other configurations of mating projections and recesses or adhesive could be used instead to affix the valve element 40 to the valve seat 22 in housing 20. The length of the short fingers 27 is less than the longitudinal length of the grooves 47 on the valve element 40 to freely permit compression of the valve element 40 during assembly without interference between the ends of the fingers 27 and the ends of the grooves 47.

Figure 3:
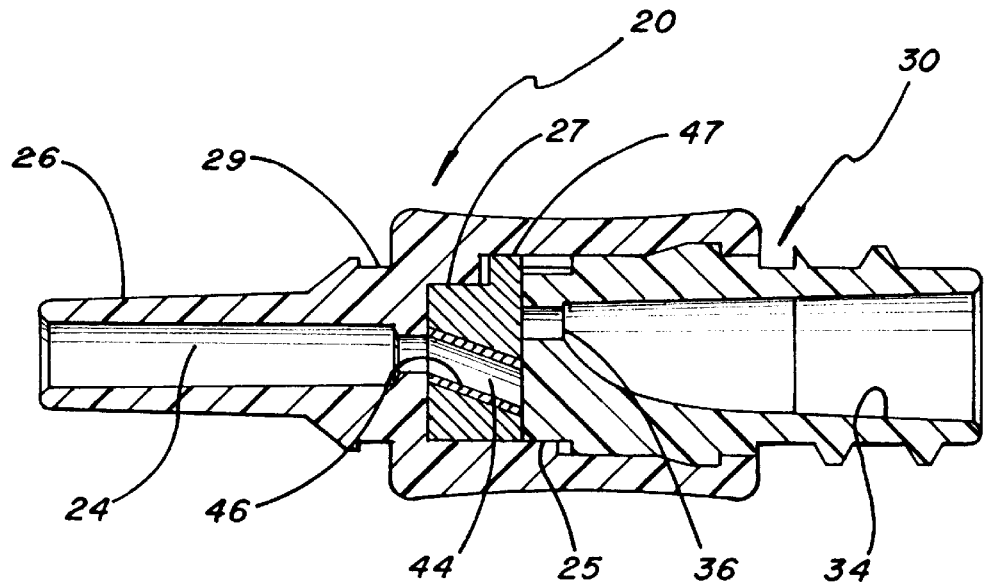
FIG. 3 comprises a longitudinal cross section view showing the medical connector with the valve element in the valve closed position.
Figure 4:
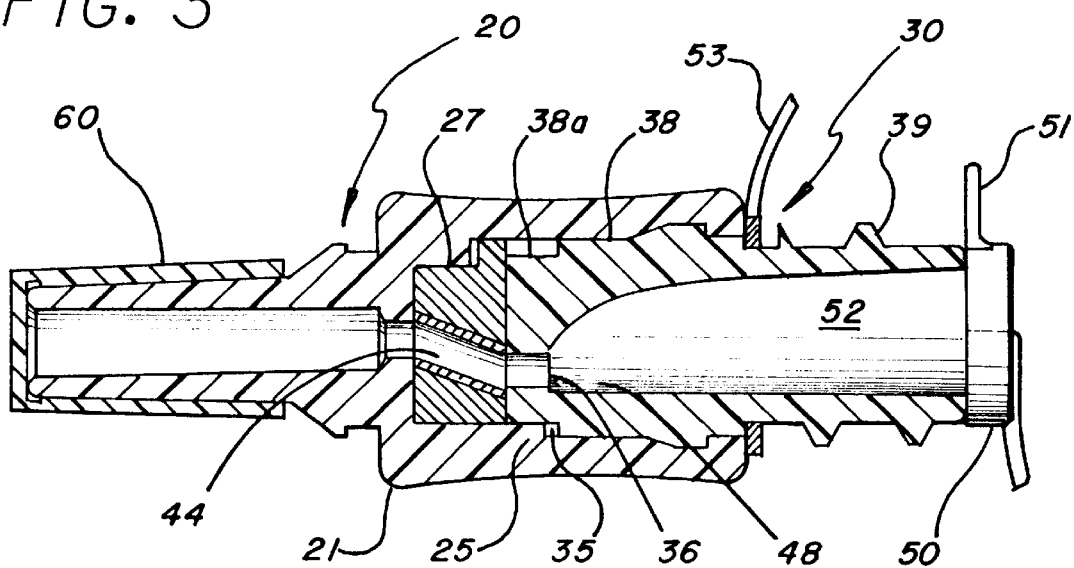
FIG. 4 is a view like FIG. 3 showing the connector in the valve open position.
Figure 6:
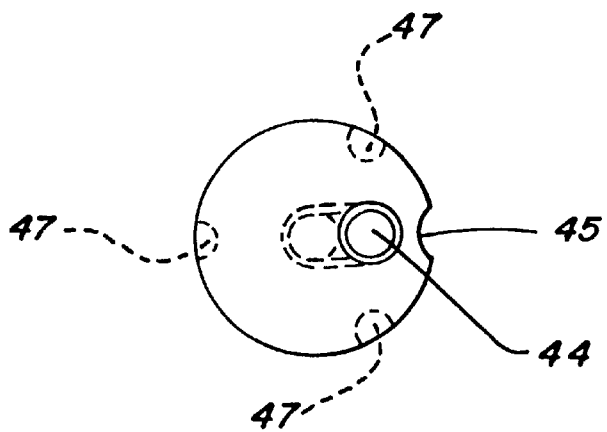
FIG. 6 is a bottom plan view of the valve element of FIG. 5.

As best seen in FIGS. 3 and 4, the off-center end 48 of the flow passageway 44 through the valve element 40 is positionable in either a valve closed position (FIG. 3) or a valve open position (FIG. 4) upon rotation of the valve actuator 30 through an angle of somewhat less than 180° relative to the housing 20.

As shown, the valve actuator 30 has a female Luer tapered receptacle with external threads 39 thereon and the housing 20 has a male tapered Luer flowline connection end 26 provided with a restraining groove 29 for receiving an annular boss on a conventional internally threaded fluid connector line swivel (not shown) which permits threaded connections to a flow line to be made or broken without twisting of the flowline. Preferably, the actuator 30 and the housing 20 are formed of medical grade polycarbonate and the valve element 40 is preferably formed of medical grade polyisoprene.

Either or both of a removable plastic plug 50 which also fulfills the functions of a cleansing swab, and a male end Luer contamination cap 60 may optionally be provided for sealing opposite ends of the medical connector during shipment or otherwise. Plug 50 has a finger grip tab 51 and a male tapered end 52 of variable diameter and length which is formed of a soft plastic and is snugly received in tapered female Luer passageway 34 such that plug 50 may be manually rotated during insertion into passage 34 to swab the passageway all the way to opening to passage 36 with alcohol after disconnection of actuator 30 from an associated flowline. Finger tab 51 permits the plug 50 to be gripped without contamination of the tapered end 52. A plastic tie loop 53 integrally formed with the plug 50 removably affixes the plug to the actuator 30. It will be noted that disconnection of the connector requires counterclockwise rotation of the female threaded line receptacle relative to the actuator 30. The connector is configured such that counterclockwise rotation first causes the actuator 30 to move to the valve closed position before further counterclockwise rotation removes the flowline connector from the conventional clockwise threads 39. Alternatively, the flowline connections can be made or broken by longitudinal insertion or removal of male or female flowline Luer connectors from the female passageway 34 or the male end 26.

The medical connector described and claimed herein is particularly advantageous in that it does not involve the use of any sharp pointed objects such as needles or cannulas. The longitudinally elongated configuration of the connector makes it particularly useful as a replacement for stopcock connectors on a manifold because the radially protruding handle of a stopcock frequently is positioned too close to an adjoining stopcock handle for easy manipulation without interference.

Figure 9:
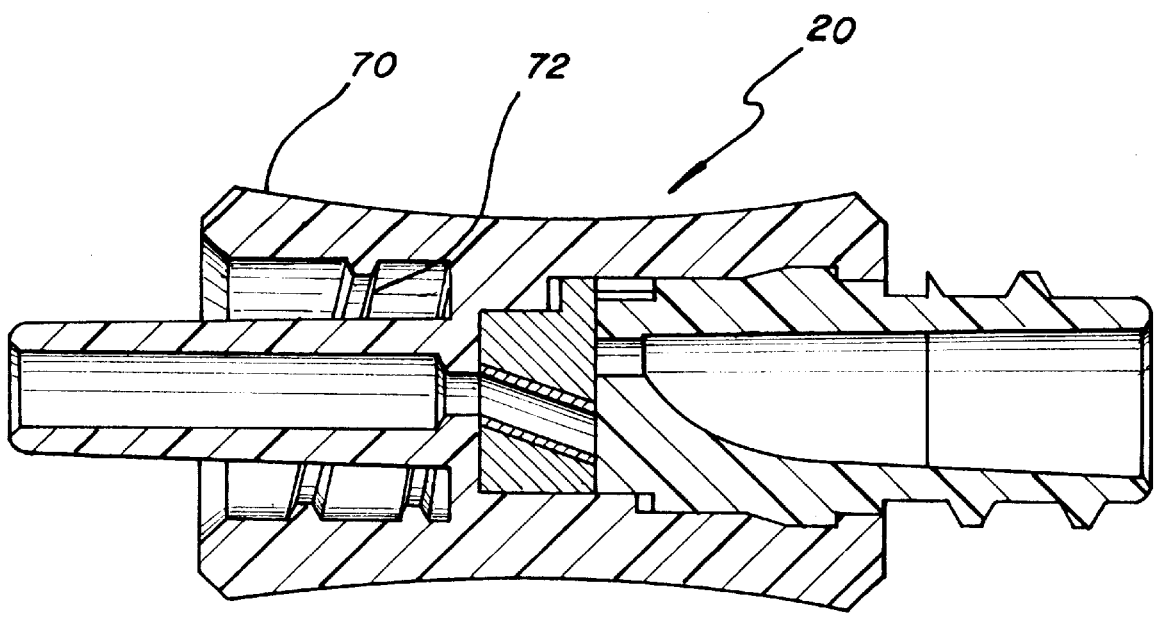
FIG. 9 is a longitudinal cross section view like FIG. 3 showing a modified housing configuration.
Figure 10:
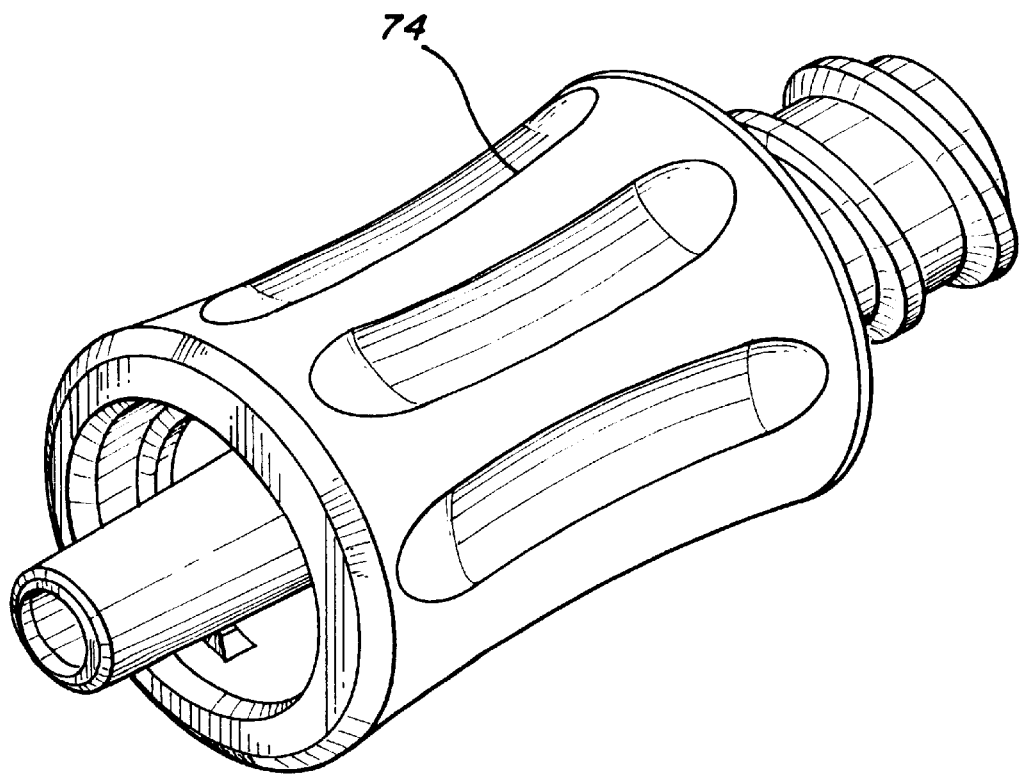
FIG. 10 is a perspective view of a medical connector having the modified housing configuration of FIG. 8.

FIGS. 9 and 10 show a modified housing 20 having an integrally formed internally threaded skirt portion 70 provided with internal threads 72 for receiving a flowline coupling to form a male Luer lock. Housing 20 may also be provided with longitudinally extending non-slip grooves 74 on the exterior of the concave finger gripping exterior surface.

While the foregoing constitutes a complete description of the preferred embodiment, it will be appreciated by persons skilled in the art that modifications can be made from the preferred embodiment and the scope of protection is to be evaluated solely with respect to the attached claims. For example, the valve element 40 may instead be non-rotatably affixed to the end of the valve actuator 30 and the eccentric end 45 of the flow passage through the valve element can face the housing 20 rather than face the actuator 30.

I claim:

1. A needle-less Luer actuated medical connector having a longitudinal axis, said connector comprising:
    A) a valve housing having a fluid flow passage therein aligned with said longitudinal axis, a valve seat therein, an open end for receiving a compressible valve element and a connection end for connecting said connector to a fluid flow line aligned with said longitudinal axis;
    B) a valve actuator having a fluid flow passage therein aligned with said longitudinal axis of said connector, a valve compressing end wall received in said open end of said housing, and a fluid flow passage extending through said end wall, said valve actuator being mounted in said open end of said housing for rotation about said longitudinal axis with respect to said housing;
    C) a resilient valve element compressed between said valve seat and said valve compressing end of said actuator, said valve element having a fluid passageway therethrough extending from an axially aligned opening on a first side of said valve element to an off-center positioned opening on an opposite side of said valve element; said off-center positioned opening of said fluid passageway in said valve element being aligned with one of (1) an off-center positioned end of said flow passageway in said valve actuator or (2) an off-center positioned end of said flow passageway in said housing when said actuator is rotated relative to said housing to open said valve and said off-center positioned end of said valve passageway being circumfrentially displaced from (1) said off-center positioned end of said flow passageway in said valve actuator or (2) said off-center positioned end of said flow passageway in said housing when said actuator is rotated relative to said housing to close the valve;
    D) means connecting said valve element to said housing to prevent relative rotation between said valve element and said housing;
    E) positioning means on said actuator and said housing to hold said actuator in either a valve open position or in a valve closed position relative to said housing; and
    F) restraining means on said housing and on said actuator for restraining relative axial movement therebetween while permitting relative rotation therebetween.

2. The medical connector of claim 1, wherein said valve seat in said housing has a fluid passageway therein axially aligned with said axially positioned opening of said fluid passageway in said valve element.

3. The medical connector of claim 2, wherein said connecting means for preventing relative rotation comprises interengaging fingers and grooves on said housing and said valve element.

4. The medical connector of claim 3, wherein said fingers are axially extending fingers on said housing and said grooves are axially extending grooves on said valve element, said grooves having an axial length less than the axial thickness of said valve element and said fingers have a length less than the axial length of the grooves to permit compression of said valve element during assembly.

5. The medical connector of claim 3, wherein said valve actuator has an end wall which compressively engages said valve element, said end wall of said actuator having an off-center positioned flow passageway therein alignable upon relative rotation of said housing and said actuator with said off-center positioned end of said flow passage in said valve element to open said valve.

6. The medical connector of claim 5, wherein said positioning means comprises an axially extending finger on a cylindrical interior wall of said housing and two axially extending grooves on a cylindrical exterior wall of said actuator proximate said valve compressing end.

7. The medical connector of claim 6, wherein said grooves on said wall of said actuator are spaced less than 180° from each other and further comprising an axially extending recess in said cylindrical wall of said actuator between said grooves, said recess having approximately the same depth as the depth of said grooves, and radially extending protuberances between said grooves and said recess.

8. The medical connector of claim 7, wherein said restraining means comprises an elastically engaging annular bulge and a bulge receiving groove on said housing and said valve actuator.

9. The medical connector of claim 8, wherein said bulge is formed on an exterior cylindrical surface of said actuator and said bulge receiving groove is formed on an interior cylindrical surface of said housing.

10. The medical connector of claim 9, wherein said bulge and said bulge receiving groove each have abutting radially extending annular shoulders to maintain axial compression of said valve element and to prevent axial disengagement of said housing and said actuator.

11. The medical connector of claim 10, wherein said valve element is axially compressed and radially expanded into sealing engagement with interior walls of said housing during assembly of the connector.

12. The medical connector of claim 11, further comprising a rigid sleeve in said flow passageway in said valve element to prevent reduction of the flow cross section during compression of the valve element.

13. The medical connector of claim 10, further comprising a concave circular cylindrical exterior finger gripping surface on said housing.

14. The medical connector of claim 10, wherein said housing includes a male Luer flowline connector thereon.

15. The medical connector of claim 10, wherein said valve actuator further comprises a female Luer flowline connector.

16. The medical connector of claim 15, further comprising an external flowline connector thread on said female Luer flowline connector opposite said valve compressing end to form a female Luer lock connector.

17. The medical connector of claim 14, wherein said male Luer flowline connector has an annular groove thereon for receiving and restraining a fluid flow line swivel connector.

18. The medical connector of claim 1, wherein said actuator and said housing are formed of medical grade polycarbonate and said valve element is formed of medical grade polyisoprene.

* * * * *